US008136283B1

(12) United States Patent
Lewis

(10) Patent No.: US 8,136,283 B1
(45) Date of Patent: Mar. 20, 2012

(54) VEHICLE IDENTIFICATION CARD WITH TRANSFERRABLE IDENTIFICATION

(75) Inventor: Mark W. Lewis, Greenville, SC (US)

(73) Assignee: Marjen, Inc., Greenville, SC (US)

( * ) Notice: Subject to any disclaimer, the term of this patent is extended or adjusted under 35 U.S.C. 154(b) by 105 days.

(21) Appl. No.: 12/267,848

(22) Filed: Nov. 10, 2008

(51) Int. Cl.

| | |
|---|---|
| ***G09F 15/00*** | (2006.01) |
| ***G09F 3/14*** | (2006.01) |
| ***A44B 15/00*** | (2006.01) |
| ***A61B 5/117*** | (2006.01) |
| ***A61B 5/103*** | (2006.01) |
| ***A44C 5/00*** | (2006.01) |

(52) U.S. Cl. ................ 40/673; 40/633; 40/665; 40/634; 40/6; 40/299.01; 283/61; 283/62

(58) Field of Classification Search .................... 40/673, 40/633, 665, 674, 634, 6, 299.01; 235/487; 283/61, 62

See application file for complete search history.

(56) References Cited

U.S. PATENT DOCUMENTS

| | | | | |
|---|---|---|---|---|
| 2,578,548 | A | 12/1951 | Histed | 40/665 |
| 4,846,501 | A | 7/1989 | Del Grande | 282/9 R |
| 4,907,359 | A | 3/1990 | Berman | 40/299 |
| 5,104,148 | A * | 4/1992 | Neal | 283/81 |
| 5,560,657 | A | 10/1996 | Morgan | 283/80 |
| 5,782,497 | A | 7/1998 | Casagrande | 283/110 |
| 6,250,556 | B1 * | 6/2001 | Schneider | 235/487 |
| 6,352,287 | B2 | 3/2002 | Casagrande | 283/81 |
| 6,352,608 | B1 | 3/2002 | Garden | 156/249 |
| 6,649,238 | B2 * | 11/2003 | Chess et al. | 428/40.1 |
| 7,246,459 | B2 * | 7/2007 | Lewis | 40/673 |
| 7,249,432 | B2 | 7/2007 | Lewis | 40/673 |
| 7,316,088 | B1 * | 1/2008 | Lewis | 40/634 |
| 7,373,749 | B1 | 5/2008 | Lewis | 40/673 |
| 2003/0106250 | A1 | 6/2003 | Best et al. | 40/674 |
| 2004/0026916 | A1 | 2/2004 | Thompson et al. | 283/61 |
| 2005/0236832 | A1 | 10/2005 | Best et al. | 283/74 |
| 2006/0163868 | A1 * | 7/2006 | Baumann | 283/66.1 |
| 2006/0236578 | A1 * | 10/2006 | Saint et al. | 40/633 |

* cited by examiner

*Primary Examiner* — Joanne Silbermann
*Assistant Examiner* — Syed A Islam
(74) *Attorney, Agent, or Firm* — Amy Allen Hinson; Nexsen Pruet, LLC

(57) ABSTRACT

A three segment vehicle identification card is provided with an upper hang tag segment, and intermediate claim ticket segment and a lower key tag segment. The lower segment has a removable key tag with a vehicle identification number together with a pair of removable labels, one of which has the vehicle identification number and the other of which has space for entry of the parking space location number for the vehicle receiving service. The removable key tag also has spaces on its foldable tail for entry of the vehicle owners name and the parking space number for the serviced vehicle.

17 Claims, 2 Drawing Sheets

VEHICLE IDENTIFICATION CARD WITH TRANSFERRABLE IDENTIFICATION

BACKGROUND OF THE INVENTION

Businesses concerned with parking or servicing vehicles have a problem of correlating the ignition key and the vehicle owner with a particular vehicle. Paper cards with three segments separated by perforations and carrying the same number have been previously provided by the inventor so that one segment serves as a claim check, a second segment is placed in the vehicle and a third segment has a key tag. One such vehicle identification card is shown in applicant's U.S. Pat. No. 7,373,749 issued May 20, 2008 for a Vehicle Identification Card with Removable Key Tag. Some businesses prefer to use key tags supplied by other suppliers. Thus there is a need to facilitate the customers use of such arrow shaped key tags from other suppliers when using the beforementioned three section vehicle identification card of inventors design.

BRIEF DESCRIPTION OF THE INVENTION

A three segment automotive vehicle locator card is formed from a thick sheet of pliable paperboard material. The three segments are established by horizontally spaced perforations or slits which permit the segments to be easily separated from one another. A large upper segment of the card includes a punched out hole and a slit from the hole to the upper edge of the card which permits the upper segment to be attached to the rear view mirror bracket of the vehicle. A second segment is a customer's claim check or ticket. The third segment of the card includes a removable key tag, a removable vehicle identification label and a removable label with a space for entering the parking space location. The same vehicle identification number is printed on the first and second segments and on the removable key tag and the vehicle identification label of the third segment. The removable key tag, the vehicle identification label and the parking space label are held in place on the third segment by adhesive. Customers, who prefer to use a key tag other than that provided on the third segment, can place the vehicle identification label and the parking space identification label on the key tag of their choice. Instructions for applying the before mentioned labels to the customers key tag are included on the third segment.

BRIEF DESCRIPTION OF THE DRAWINGS

The invention is illustrated in the accompanying drawings, in which.

DETAILED DESCRIPTION OF THE INVENTION

Figure 1:
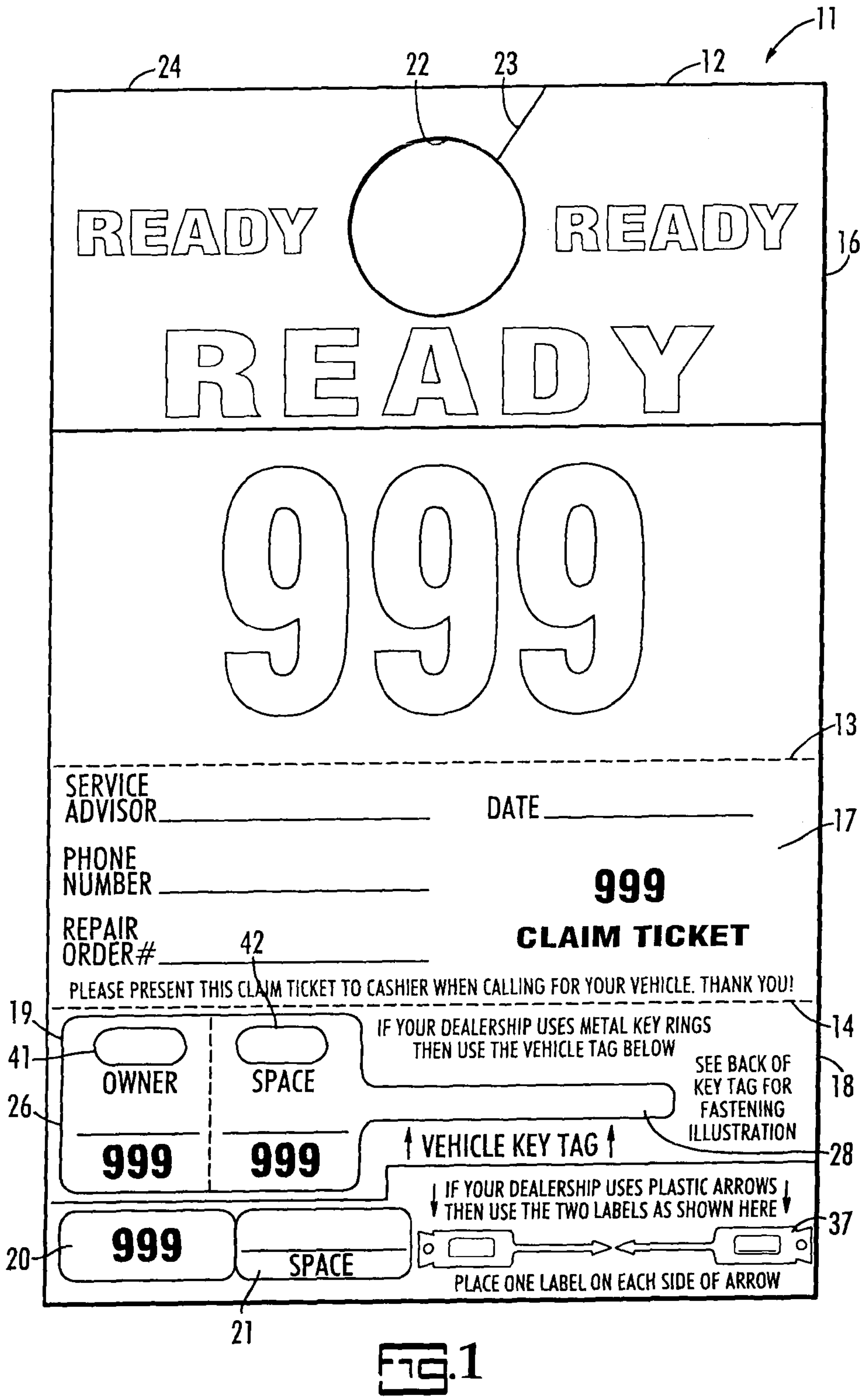
FIG. 1 shows the front or ready side of a vehicle identification and locator card and FIG. 2 shows the rear or service side of the card shown in FIG. 1.
Figure 2:
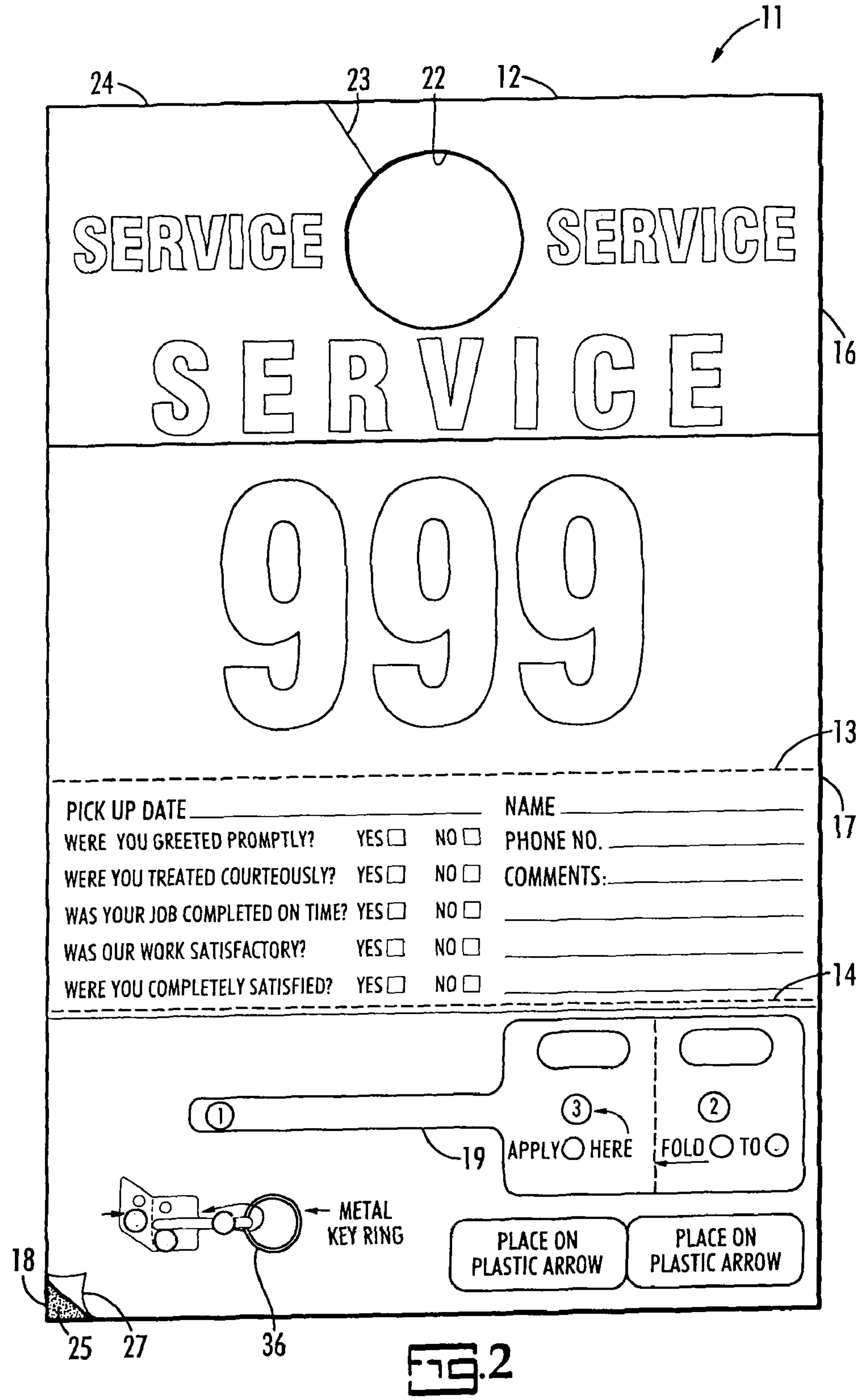

The vehicle locator card 11 shown in the drawings includes a relatively thick pliable paperboard sheet 12 which is perforated along horizontal lines 13 and 14 to form an upper segment 16, an intermediate claim ticket segment 17 and a lower segment 18 in which a key tag 19, a vehicle identification label 20 and a parking space label 21 are formed. A rubber based permanent adhesive 25 is applied to the rear side of the third segment 18 and a 40 pound silicone coated translucent kraft liner patch 27 is attached to the rear side of the third segment 18. The upper segment 16 includes a punched out hole 22 near its upper edge and a slit 23 between the hole 22 and the upper edge 24 of the segment 16 permitting the upper segment 16 to be hung in the vehicle—such as on a rear view mirror support. The perforations along lines 13 and 14 permit relatively easy separation of the segments 16, 17, 18 from one another. The front of the upper and intermediate segments 16, 17 carry the vehicle identification number. The vehicle identification number is printed twice on the tail of the key tag 19 so that when it is folded in half to capture the head 28 that has been passed through the key ring, as shown in FIG. 2; the vehicle identification number will show on both sides of the vehicle key tag 19. Underlined spaces above the vehicle identification numbers on the tail, identified by the words owner and space are available for entering the vehicle owner's name and the vehicle parking space number. The identification labels 20, 21, upon being removed from segment 18, are attachable by the permanent adhesive on their back side to opposite sides of a key tag of customers choice, as illustrated in FIG. 1.

The outline of the key tag 19, the outline of the identification labels 20, 21 and the outline of the oval shaped holes 41, 42 are formed by a die cuts punched through the card 12 but not through the patch 27. When the key tag 19 or the identification labels 20, 21 are removed, the permanent adhesive 25 releases from the smooth surface silicone coated translucent patch 27 and remains on the removed key tag 19 and identification labels 20, 21. The front of the upper and intermediate segments 16, 17 carry the vehicle identification number. The claim number and the vehicle identification number as the same. The vehicle identification number is printed twice on the tail of the key tag 19 so that when it is folded in half to capture the head 28 that has been passed through the key ring, as shown in FIG. 2, the vehicle identification number will show on both sides of the vehicle key tag 19. Spaces above the vehicle identification numbers on the tail, identified by the words owners and space, are available for entering the vehicle owner's name and the vehicle parking space number.

A business using the vehicle location card 11 may use the vehicle key tag 19 by attaching it directly to an ignition key or indirectly to an ignition key, such as by attachment to a key ring 36 as shown in FIG. 2. If the vehicle servicing business prefers to use other style key holders, such as the plastic arrow 37 shown in FIG. 1, the labels 20, 21 are placed on opposite sides of the tail of the arrow 37.

Many businesses purchasing the vehicle identification cards have branch facilities and a central administration which handles purchasing and stocking of supplies. This novel vehicle identification card permits the branch facilities to use key rings and key holders of their choice with the herein described standardized vehicle identification card, thereby retaining the economy of mass purchasing of the identification card. Providing designated places for entering the vehicle owners name and the parking space location on the vehicle key helps servicing personnel to quickly find and retrieve the vehicle for the customer.

What is claimed is:

1. A vehicle identification card, comprising:

a sheet of paperboard having a front side and a rear side, said sheet being divided by perforations into an upper segment serving as a hang tag, an intermediate segment serving as a customer's claim ticket and a lower segment separable from the upper and intermediate segments, a layer of permanent adhesive on the rear side of only said lower segment, a silicone coated patch adhered to said rear side of only said lower segment, said layer of permanent adhesive between said sheet and said silicone coated patch, a die cut through said lower segment of said paperboard forming a removable elongated key tag having a narrow head and a wide foldable tail for capturing said narrow head there between and a pair of removable labels, said upper segment, said intermediate segment, said tail of said key tag and one of said removable labels having the same vehicle identification number imprinted thereon.

2. The vehicle identification card of claim 1 wherein said pair of removable labels are positioned below said tail of said key tag.

3. The vehicle identification card of claim 1 wherein said tail of said key tag is foldable in half to adhesively capture said narrow head, and wherein each foldable half includes said vehicle identification number which is visible when said tail is folded in half to capture said head of said key tag.

4. The vehicle identification card of claim 3 wherein said folded halves of said tail of said key tag have designated spaces for entry of a vehicle owner's name and a vehicle parking space, respectively.

5. The vehicle identification card of claim 1 wherein one of said removable labels carries said vehicle registration number and the other of said labels has a designated space for entry of the parking space of the identified vehicle.

6. The vehicle identification card of claim 5 wherein said tail of said key tag is foldable in half to adhesively capture said narrow head and wherein said foldable halves have designated spaces for entry of a vehicle owner's name and the parking space occupied by the owner's vehicle.

7. The vehicle identification card of claim 1 wherein said patch adhered to the rear side of said lower segment includes instructive information for said key tag and said pair of removable labels.

8. The vehicle identification card of claim 1 wherein said foldable tail is foldable along a centerline perpendicular to said narrow head.

9. The vehicle identification card of claim 1 wherein said tail of said key tag comprises an opening therein.

10. The vehicle identification card of claim 1 wherein said layer of permanent adhesive and said silicone coated patch cover the entire rear side of said key tag.

11. The vehicle identification card of claim 1 wherein said tail of said key tag comprises two openings wherein when said tail is folded said openings overlap.

12. A vehicle identification card, comprising:

a sheet of paperboard having a front side and a rear side, said sheet being divided by perforations into an first segment serving as a hang tag, an second segment serving as a customer's claim ticket and a third segment separable from the first and second segments, a layer of permanent adhesive on the rear side of said third segment, a silicone coated patch adhered to said rear side of said third segment, said layer of permanent adhesive between said sheet and said silicone coated patch, and a die cut through said third segment of said paperboard forming a removable elongated key tag having a narrow head and a wide foldable tail for capturing said narrow head there between, said wide foldable tail of said key tag including two openings wherein when said tail is folded said openings overlap, said first segment, said second segment, and said tail of said key tag having the same vehicle identification number imprinted thereon.

13. The vehicle identification card of claim 12 wherein said openings are perforated.

14. The vehicle identification card of claim 12 wherein said third segment includes a pair of removable labels.

15. The vehicle identification card of claim 12 wherein said tail of said key tag is foldable in half to adhesively capture said narrow head, and wherein each foldable half includes said vehicle identification number which is visible when said tail is folded in half to capture said head of said key tag.

16. The vehicle identification card of claim 12 wherein said foldable tail is foldable along a centerline perpendicular to said narrow head.

17. The vehicle identification card of claim 12 wherein said layer of permanent adhesive and said silicone coated patch cover the entire rear side of said key tag.

* * * * *